United States Patent
Baldwin et al.

(10) Patent No.: US 7,038,054 B1
(45) Date of Patent: May 2, 2006

(54) DIAZABICYCLONONANE SCAFFOLD FOR COMBINATORIAL SYNTHESIS

(75) Inventors: John J. Baldwin, Gwynedd Valley, PA (US); Vinh D. Tran, North Brunswick, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 454 days.

(21) Appl. No.: 10/166,833

(22) Filed: Jun. 11, 2002

Related U.S. Application Data

(62) Division of application No. 09/652,178, filed on Aug. 31, 2000, now abandoned.

(60) Provisional application No. 60/152,252, filed on Sep. 3, 1999.

(51) Int. Cl.
*C07D 471/02* (2006.01)

(52) U.S. Cl. ...................... 546/122; 514/300
(58) Field of Classification Search ................ 546/122; 514/300
See application file for complete search history.

(56) References Cited

U.S. PATENT DOCUMENTS

| | | | | |
|---|---|---|---|---|
| 3,962,449 | A * | 6/1976 | Binnig et al. | 514/300 |
| 4,556,662 | A | 12/1985 | Binnig et al. | 514/300 |
| 4,959,373 | A * | 9/1990 | Lubisch et al. | 514/300 |
| 5,677,311 | A | 10/1997 | Miyazawa et al. | 514/299 |
| 6,291,475 | B1 * | 9/2001 | Alstermark et al. | 514/300 |

FOREIGN PATENT DOCUMENTS

WO    WO 9931100 A1 *    6/1999

OTHER PUBLICATIONS

Fernandez et al. Journal of Molecular Structure (1995), 355(3): 229-238.*
Miyazawa, CA 123:169517, abstract of CA 2128493, 1995.*
Farina, CA 128:140612, abstract of WO 9801443, 1998.*
Fernandez, CA 124:164269, abstract of J of Molecular Structure, vol. 372(2-3), pp. 203-213, 1995.*
Fernandez, CA 124:29044, abstract of J of Molecular Streructure, vol. 355(3), pp. 229-238, 1995.*
Fernandez et al. "Structural conformational, biochemical, and pharmacological . . . " *J. Molecular Structure 372*, 203-213 (1995).
Fernandez et al. "Synthesis and structural and conformational study of some amides . . . " *J. Molecular Structure 355*, 229-238 (1995).

* cited by examiner

*Primary Examiner*—D. Margaret Seaman
(74) *Attorney, Agent, or Firm*—Heslin Rothenberg Farley & Mesiti, P.C.; Philip E. Hansen

(57) ABSTRACT

Diazabicyclononanes of formula I and their synthesis

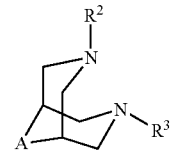

are disclosed. The compounds are useful as scaffolds for constructing combinatorial libraries.

8 Claims, No Drawings

DIAZABICYCLONONANE SCAFFOLD FOR COMBINATORIAL SYNTHESIS

CROSS REFERENCE TO RELATED APPLICATIONS

This application is a divisional of U.S. application Ser. No. 09/652,178, filed Aug. 31, 2000, now abandoned, which claims the benefit of Provisional Application No. 60/152,252, filed Sep. 3, 1999, the entire disclosure of which is incorporated herein by reference.

FIELD OF THE INVENTION

The invention relates to diazabicyclononanes, to their synthesis and to their use as templates for the construction of combinatorial libraries.

BACKGROUND OF THE INVENTION

Combinatorial organic synthesis is becoming an important tool in drug discovery. Methods for the synthesis of large numbers of diverse compounds have been described [Ellman, et. al. *Chem. Rev.* 96: 555–600 (1996)], as have methods for tagging systems [Ohlmeyer et al., *Proc. Natl. Acad. Sci.* USA, 90, 10922–10926, (1993)]. The growing importance of combinatorial synthesis has created a need for molecules which can be readily elaborated into libraries by simple and readily variable chemistry. Because the literature abounds with methods for fashioning amide bonds and with methods for protecting nonreacting groups from the chemical transformations induced by reagents for fashioning amide bonds, molecules that offer differentiable amines are of great utility as so-called scaffolds for combinatorial synthesis.

Receptors are molecules which selectively interact with other molecules. Antibodies, which represent one class of naturally occurring receptor molecules, bind to other molecules (antigens) with very high selectivity; they are also known to catalyze chemical reactions by selectively binding the transition states. Monoclonal antibodies are used as medicinal and diagnostic agents. Although antibodies are proteins, all receptor molecules need not be proteins. Receptor molecules perform a variety of tasks from selective binding of substrates to catalyzing chemical reactions, and their effectiveness is dependent upon their ability to bind molecular species (substrates or acceptors) with high selectivity. For example, the free energy for an antibody binding its antigen is normally from 6–15 kcal/mol.

There is considerable interest in synthetic receptors and libraries thereof. For example, Still et al. (U.S. Pat. No. 5,804,563 and PCT US95/00572) have described synthetic receptors which comprise a polyfunctional organic template covalently linked to two or more oligomers. In Still's case, as well as in the present invention, the oligomers may be oligoamides, oligoesters, oligoureas, oligourethanes, oligoamines, oligoethers, oligosulfonamides, oligonucleotides, oligosaccharides, peptides, etc.

In the construction of a library, a template or scaffold (the two will be used interchangeably herein) may be linked to a solid substrate and to an identifier which uniquely defines the synthetic receptor. The identifier is a stable chemical molecule or a plurality of stable chemical molecules distinguishable and detectable to picomolar levels. Usually the template is covalently linked to a solid support which is in turn covalently linked to the identifier, but in some embodiments the template may be directly attached to the identifier. (See PCT application WO 95/19567.)

Throughout this application, various references are referred to within parentheses or square brackets. The disclosures of these publications in their entireties are hereby incorporated by reference into this application. Variables are defined when introduced and retain that definition throughout. The term "combinatorial library" refers to a collection of molecules based on logical design and involving the selective combination of building blocks by means of simultaneous chemical reactions. Each species of molecule in the library is referred to as a member of the library.

SUMMARY OF THE INVENTION

In one aspect, the invention relates to diazabicyclononanes (also known as bispidines) of formula I

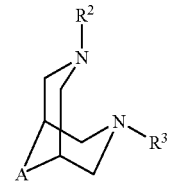

wherein A is C=O or CH—NHR$^1$;

R$^1$ is hydrogen or the residue of a solid substrate;

R$^2$ is hydrogen or a first amino-protecting group;

R$^3$ is hydrogen or a second amino-protecting group, with the proviso that no more than one of R$^1$, R$^2$ and R$^3$ is hydrogen. A single amino-protecting group cannot function as both the first amino-protecting group and the second amino-protecting group, i.e. R$^2$ and R$^3$ cannot be the same. The compounds are useful as scaffolds or templates for constructing combinatorial libraries, for constructing synthetic receptors and for constructing combinatorial libraries of these receptors.

In another aspect the invention relates to preparing a combinatorial library, said method comprising the steps of:

(a) coupling a compound of formula

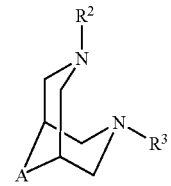

, wherein A is CH—NH$_2$, to a solid substrate to provide a substrate-linked template having two protected active sites. In these compounds, R$^2$ is a first amino-protecting group, R$^3$ is a second amino-protecting group and R$^2$ and R$^3$ are orthogonally removable. The substrate-linked template is then (b) reacted with an activator to remove a first protecting group therefrom to expose a first active site, followed by (c) coupling an amine-reactive moiety to the exposed first active site; (d) reacting the substrate-linked template with an activator to remove a second protecting group therefrom to expose a second active site; and (e) coupling an amine-reactive moiety to the exposed second active site. The amine-reactive moieties may include the oligomers of Still, noted above. The method may include the additional step of coupling an identifier to the solid substrate between steps (c) and (d).

In another aspect, the invention relates to a process for synthesizing a diazabicyclononane of formula

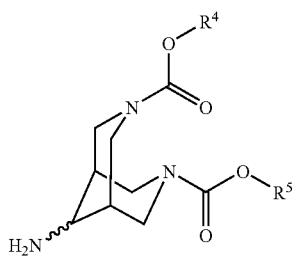

wherein $R^4$ is t-butyl or allyl, $R^5$ is t-butyl or allyl and $R^4 \neq R^5$; comprising (a) reacting 1-benzyl-4-piperidone with α-methylbenzylamine, paraformadehyde and acetic acid to provide a differentially protected diazabicyclononanone of formula

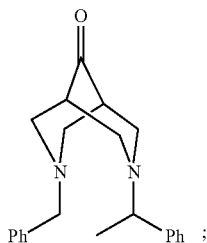

(b) selectively cleaving the α-methylbenzyl group from one amine to provide an aminoketone;

(c) reacting the aminoketone with a precursor to a urethane to provide a keto-urethane of formula

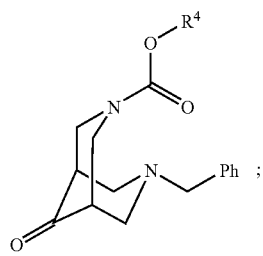

(d) selectively cleaving the benzyl group from the keto-urethane to provide a second aminoketone;

(e) reacting the second aminoketone with a precursor to a urethane to provide a keto-diurethane of formula

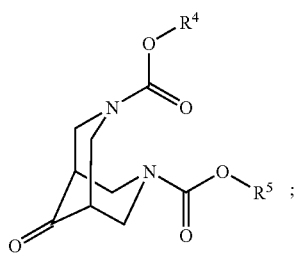

and (f) reductively aminating the keto-diurethane. Preferably, $R^4$ is t-butyl and $R^5$ is allyl.

DETAILED DESCRIPTION OF THE INVENTION

The invention relates to compounds of formula I

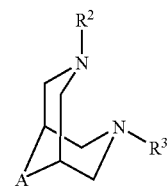

A preferred subset of the genus includes compounds wherein A is CH—NH$_2$, particularly those in which $R^2$ and $R^3$ are chosen from t-butoxycarbonyl, allyloxycarbonyl, benzyloxycarbonyl, fluorenylmethoxycarbonyl, benzyl and α-phenylethyl. Preferred embodiments of the subgenus are those in which one of $R^2$ and $R^3$ is t-butoxycarbonyl and the other is chosen from allyloxycarbonyl, benzyloxycarbonyl, and fluorenylmethoxycarbonyl. This subgenus is useful for attaching to a solid substrate as a scaffold for preparing libraries.

Another preferred subset of the genus includes compounds that are intermediates in the synthesis of the foregoing subgenus. In these compounds A is C=O, one of $R^2$ and $R^3$ is hydrogen and the other is chosen from t-butoxycarbonyl, allyloxycarbonyl, benzyloxycarbonyl, fluorenylmethoxycarbonyl, benzyl and α-methylbenzyl.

In another subgenus, A is CH—NHR$^1$, R$^1$ is the residue of a solid substrate, one of $R^2$ and $R^3$ is hydrogen and the other is chosen from t-butoxycarbonyl, allyloxycarbonyl, benzyloxycarbonyl, fluorenylmethoxycarbonyl, benzyl and α-phenylethyl. Compounds in which one of $R^2$ and $R^3$ is t-butoxycarbonyl and the other is chosen from allyloxycarbonyl, benzyloxycarbonyl, and fluorenylmethoxycarbonyl are particularly preferred.

The amines are protected with any of the well-known protecting groups for amines. [See Greene and Wuts *Protective Groups in Organic Synthesis* Second Edition John Wiley & Sons, New York 1991, pages 309–370 which are incorporated herein by reference.]. The term "amino-protecting group" refers to the groups described by Greene and Wuts for amines and to similar groups for the same purpose. Orthogonal urethanes are preferred protecting groups for the amine. Methods for protecting and deprotecting with these groups are found in Greene and Wuts on pages 315–349. Orthogonal protecting groups are groups that can be selectively removed in the presence of each other. For example t-Boc is orthogonal to allyloxy in that t-Boc is cleaved by anhydrous acid, while allyloxy is stable to anhydrous acid; conversely allyloxy is cleaved by Pd(0) species in the presence of a reducing agent, while t-Boc is stable.

An "activator", as the term is used herein refers to a reagent that removes a protecting group from an amine to expose an active site, which is the free amine. Thus the activator will depend on the protecting group. Activators for deprotecting amines are found in Greene and Wuts. For example, acid would be an activator for the t-Boc group; fluoride ion would be an activator for the Fmoc group; palladium and tin hydride would be activators for allyloxy; chloroethyl chloroformate would be an activator for the α-methylbenzyl group; hydrogen and a noble metal catalyst would be activators for the benzyl group.

The preparation of a suitable solid phase for attachment to the compounds of the invention is presented in Scheme A:

An amino-functionalized resin, such as PEG-grafted polystyrene beads (e.g. TentaGel™, 5) may be modified to increase the available reaction sites for ligand attachment. Bis-Fmoc lysine, 6, is coupled to amino-functionalized TentaGel, 5, by amide bond formation. Coupling is achieved by reacting a suspension of 5 in DMF with 6, HOBt and DIC. The suspension is shaken overnight, then drained or filtered and washed in succession with DMF, MeOH and DCM. The derivatized resin 7 so obtained is dried overnight under vacuum.

The Fmoc-protecting group on resin 7 is removed and 4-bromomethyl-3-nitrobenzoic acid (BNB) is attached by the following method: A suspension of 7 in 1:1 piperidine:DMF is shaken about 1.5 hr, then washed with DMF, MeOH, DCM. The resulting diamine resin 8 is suspended in DMF, and treated with a solution of BNB, HOBt, and DIC in DMF. The suspension is shaken overnight, then drained and the resin is washed with DCM. The BNB resin 9 is dried overnight in vacuo.

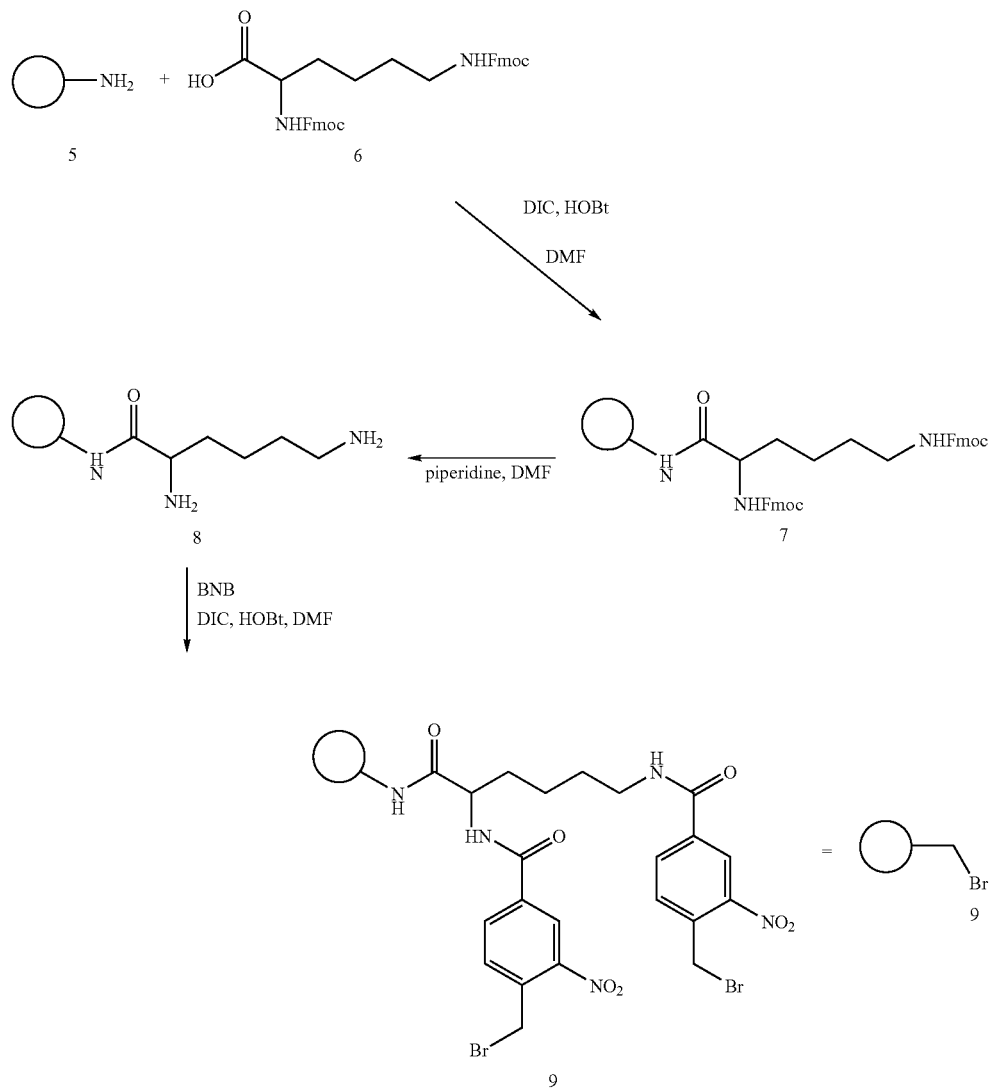

The coupling of bispidine amine 4 (synthesis described below) to the BNB resin 9 is accomplished by displacement of the linker bromide with formation of a new carbon-nitrogen bond. Two cycles of reactions are performed to ensure the complete conversion. In the first cycle, bispidine amine 4 and LiI are added to a suspension of resin 9 in DMF and the mixture is shaken overnight. The mixture is drained and the resin is washed with DMF. The DMF solution containing excess amine is then concentrated, taken up in $CH_2Cl_2$, washed with aqueous sat. $NaHCO_3$, dried ($MgSO_4$), filtered and concentrated. The residue is taken up in DMF and treated with the same resin for the second cycle. Lithium iodide is added to the suspension and the mixture is shaken overnight. The suspension is drained and the resin is washed with DMF, methanol, DCM and dried overnight in vacuum. A small portion of resin may be removed and titrated with picric acid to determine the extent of amine loading as a quality control for the reaction.

The synthesis of bispidine amine 4 and its attachment to the resin are shown in Scheme B:

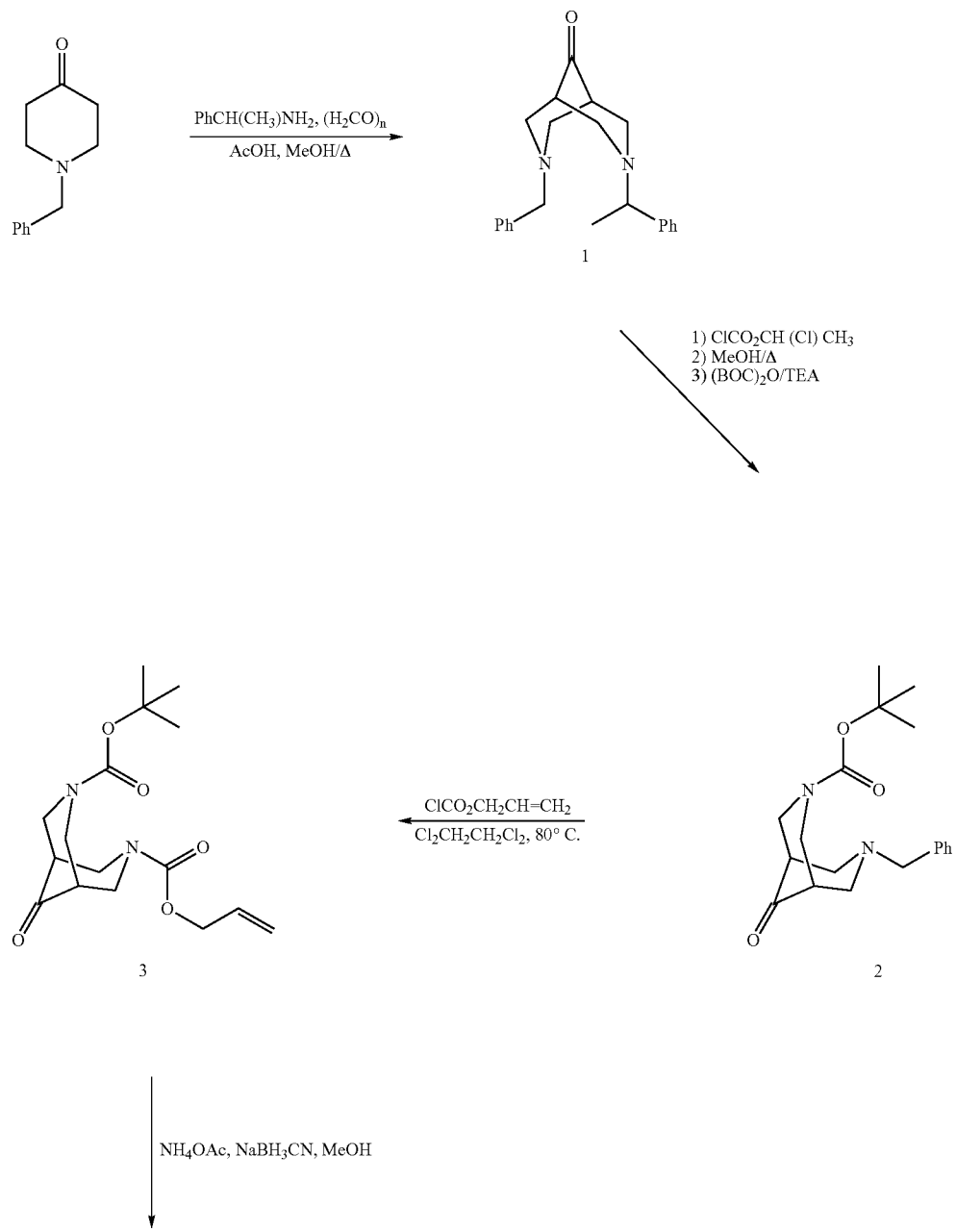

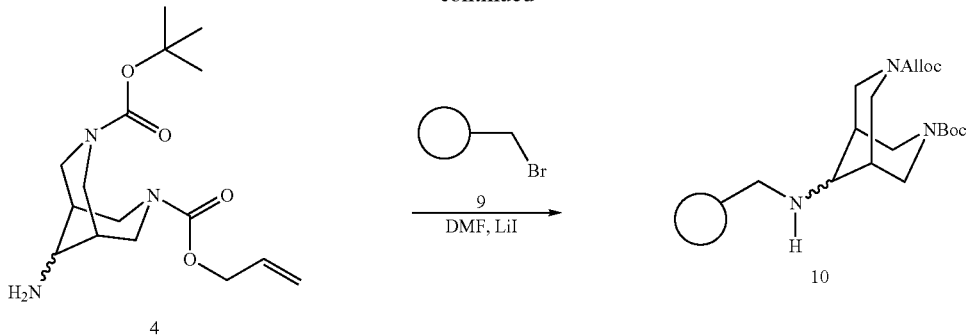

A mixture of α-methylbenzylamine (10.7 g, 0.088 mol), paraformaldehyde (21.1 g, 0.703 mol), acetic acid (10.2 mL, 0.179 mol) and 1-benzyl-4-piperidone (16.7 g, 0.088 mol) in MeOH (418 mL) was heated at reflux overnight. Upon cooling to room temperature the solvents were removed in vacuo. Water (700 mL) and KOH pellets (11.7 g, 0.209 mol) were added and the mixture was extracted with 3×150 mL CH$_2$Cl$_2$. The organic layer was dried (K$_2$CO$_3$), filtered and the solvent was removed in vacuo. The yellow residues were triturated with hexane and the combined organic solvents were concentrated to provide bispidine (1) as a crude yellow oil (26.7 g, 90%).

To a solution of crude ketone 1 (26.7 g, 0.080 mol) in 1,2-dichloroethane (80 mL) at 0° C. was added 1-chloroethyl chloroformate (8.3 mL, 0.080 mol). After 30 min the solution was heated at reflux for 45 min. The solvents were removed in vacuo and the residues were diluted with CH$_2$Cl$_2$ (80 mL), cooled to 0° C. then triethylamine (35 mL, 0.25 mol) and di-tert-butyl dicarbonate (19.1 g, 0.088 mol) were added. The resulting mixture was stirred at room temperature overnight, whereupon saturated aqueous NaHCO$_3$ (30 mL) was added. The aqueous layer was extracted with 3×50 mL CH$_2$Cl$_2$. The combined organic layers were dried (MgSO$_4$), filtered, and the solvent was removed in vacuo to provide a yellow oil, which was purified on SiO$_2$ with 3:1-hexane:EtOAc to afford 12.2 g of 2 as a clear oil.

To ketone 2 (12.2 g, 0.037 mol) in a round bottom flask was added allyl chloroformate (20 mL, 0.189 mol) and the mixture was heated at reflux for 1.5 h. Upon cooling to room temperature CH$_2$Cl$_2$ (200 mL) and sat. aqueous NaHCO$_3$ (75 mL) were added. The aqueous layer was extracted with 3×75 mL CH$_2$Cl$_2$. The combined organic layers were dried (MgSO$_4$), filtered, and the solvent was removed in vacuo to provide a yellow oil, which was purified on SiO$_2$ with 6:1-hexane:EtOAc, then 20:1:0.1-CHCl$_3$:MeOH:NH$_4$OH to afford 6.61 g of 3 as a clear oil.

A mixture of ketone 3 (3.39 g, 0.011 mol), ammonium acetate (8.1 g, 0.105 mol) and NaCNBH$_4$ (1.29 g, 0.021 mol) in MeOH (43 mL) was stirred at room temperature for 3 days. The solvents were removed in vacuo and the residues were diluted with EtOAc (150 mL) and treated with 1 N NaOH (until pH 11). The organic layer was extracted with 3×100 mL EtOAc. The combined organic layers were dried (MgSO$_4$), filtered, and the solvent was removed in vacuo to provide a residue, which was purified on SiO$_2$ with 20:1:0.1-CHCl$_3$:MeOH:NH$_4$OH to afford 1.48 g of 4 as a clear oil.

The genus of substituted bicyclononanes of the invention was employed to prepare a combinatorial library of differentially substituted bispidines as shown in the general synthesis in Scheme C:

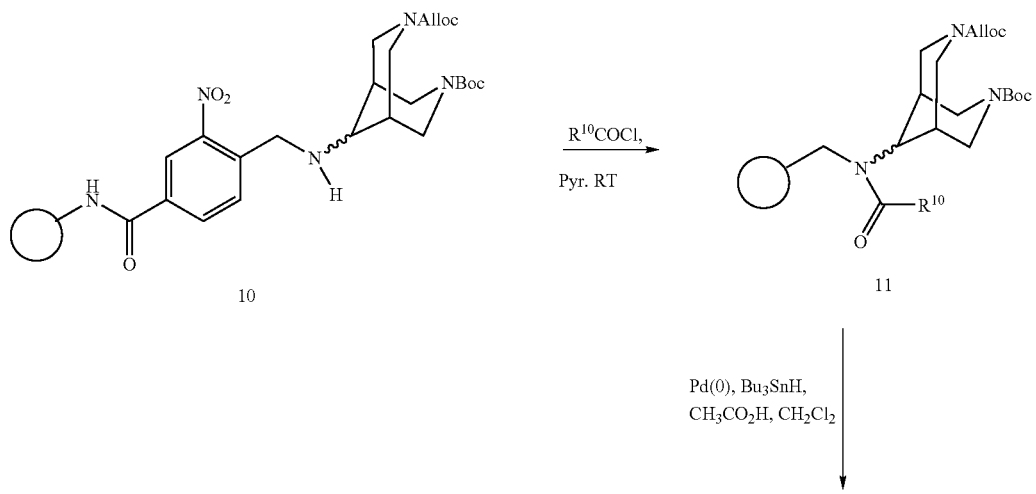

-continued

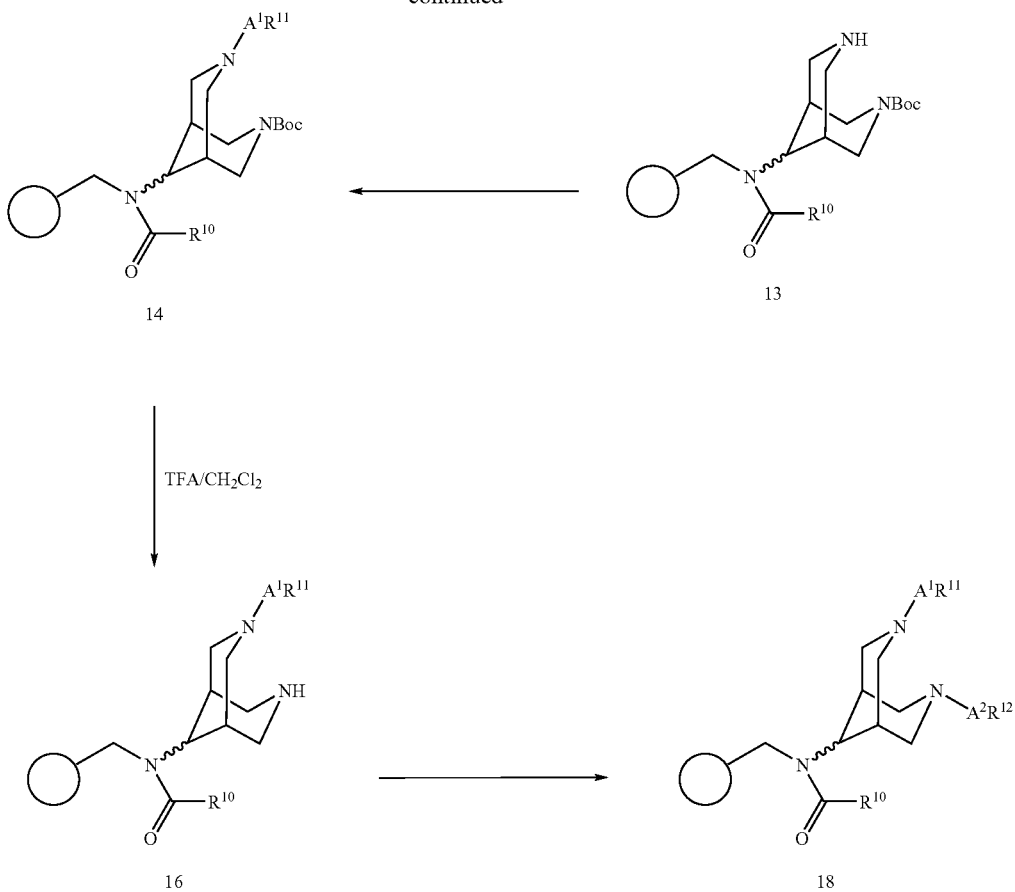

In these compounds, $A^1$ and $A^2$ are —(CH$_2$)—, —C(=O)— or —S$_2$—, and the $R^{11}A^1$ and $R^{12}A^2$ residues represent amine-reactive moieties. The term "amine-reactive moiety" refers to a substance that reacts with an amine. Amine-reactive moieties include: acid chlorides, acid anhydrides, activated esters, carboxylic acids, sulfonyl chlorides, isocyanates, aldehydes, ketones, alkyl halides, and, in general, electrophilic species. The person of skill will recognize that carboxylic acids, aldehydes and ketones do not usually, in the absence of other reagents, react with amines to produce stable products. Nonetheless, they are considered amine-reactive moieties, since, in the presence of other reagents, as described below, they react readily with amines to provide stable and useful products. Condensing agents for reacting amines with carboxylic acids are well known, particularly in the art of peptide synthesis. Such agents include carbodiimides of various sorts, mixed anhydrides, EEDQ, HATU, and the like. It is also possible to pre-react the carboxylic acid with an appropriate leaving group to form an activated ester. Activated esters denote esters which are capable of undergoing a substitution reaction with primary or secondary amines to form an amide. The term includes esters "activated" by neighboring electron withdrawing substituents. Examples include esters of phenols, particularly electronegatively substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters. Ketones and aldehydes can be reacted with amines by reductive amination in the presence of hydrogen and a catalyst, or preferably with hydride reducing agents, such as borohydrides and cyanoborohydrides.

In an exemplary series of reactions, an appropriate acid chloride $R^{10}$COCl, wherein $R^{10}$ is benzil, was added to a suspension of amine resin 10 in pyridine. The mixture was shaken overnight, drained and the resin was washed with DMF, MeOH and DCM to afford the amide-linked resin 11. The amide-linked resin 11 was placed in a reaction vessel, dichloromethane, acetic acid and tetrakis(triphenylphosphine)palladium (0) were added and the mixture was shaken for 15 min. Tributyltin hydride was added and the mixture was shaken for an additional 45 min. then drained and the resin was washed with pyridine and DCM. The secondary amino-linked resin 13 was dried overnight in vacuo. The amine, 13, was coupled with an acid or acid chloride corresponding to the appropriate residue $R^{11}$ μl [$A^1$ is —C(=O)—] by amide bond formation. This was accomplished by one of two procedures. According to a first procedure, the appropriate acid was added to the corresponding reaction vessel containing amino-linked resin 13, DIC and HOBt in DMF. The mixture was shaken overnight, drained and the amide-linked resin 14 was washed with DMF, MeOH and DCM. In an alternate procedure, the amine 13 was coupled with the corresponding acid chloride by adding the acid chloride to a suspension of amine resin 13 in pyridine. The mixture was shaken overnight, drained and the amide-linked resin 14 was washed with DMF, MeOH and DCM.

The amide-linked resin 14 was put in a reaction vessel and the Boc group was removed by adding a 30% solution of trifluoroacetic acid in dichloromethane. After shaking for 1 hour, the solution was drained and the resin was first washed with a 20% solution of triethyl amine in dichloromethane and then with dichloromethane. The secondary amino-linked resin 16 was dried over night in vacuo.

The amine, 16, was coupled with an acid chloride, acid or sulfonyl chloride corresponding to $R^{12}A^2$ [$A^2$ is —C(=O)— or —SO$_2$—]. This was accomplished by one of four procedures: According to Procedure A, an acid chloride was added to the amino-linked resin 16, dichloromethane and pyridine were added and the mixture was shaken overnight, drained and the amide-linked resin 18 was washed with DMF and DCM. According to procedure B, the appropriate acid was added to the amine 16 followed by DIC and HOBt in DMF. The mixture was shaken overnight, drained and the amide-linked resin 18 was washed with DMF, MeOH and DCM. In procedure C, the acid was added to the amine 16 followed by HATU and DIEA in DMF. The mixture was shaken overnight, drained and the amide-linked resin 18 was washed with DMF, MeOH and DCM. In procedure D, the corresponding sulfonyl chloride was added to the amine 16 followed by pyridine in DCM. The mixture was shaken overnight, drained and the amide-linked resin 18 was washed with DMF, MeOH and DCM. In each case, the triamide bispidine compounds 18 were dried overnight in vacuo.

Compounds in which $R^{11}A^1$ and $R^{12}A^2$ are substituted alkyl residues [$A^1$ or $A^2$ is —CH$_2$—] may be synthesized by reductive amination with the corresponding aldehyde. The amino-linked resin 16 is treated with the aldehyde and BH$_4$CN in MeOH:acetic acid (20:1). The mixture is shaken overnight, drained and washed with MeOH, 15% solution of K$_2$CO$_3$, H$_2$O and MeOH. The resulting bispidine compounds 18 are dried overnight in vacuo. The same reaction may be done with the amino-linked resin 13 to provide bispidine compounds 18.

The members of the library are cleaved from the solid phase support by methods well known in the art. Linkers are molecules that can be attached to a solid support and to which the desired members of a library of chemical compounds may in turn be attached. When the construction of the library is complete, the linker allows clean separation of the target compounds from the solid support without harm to the compounds and preferably without damage to the support. A number of linkers have been described in the literature [Backes et al., *Current Opinion in Chemical Biology* 1, 86–93 (1997)]. In the examples above in which the bicyclononane is attached to the resin by a nitrobenzyl linker, the diazabicyclononane is cleaved by exposure to UV light (ca. 360 nm) for 15–180 minutes at 25–50° C. in a suitable solvent such as methanol. Alternatively, one may employ a 4-[4-(formyl)-3,5-dimethoxyphenoxy]butyryl residue as linker. It is attached to a solid phase substrate via the carboxyl of the butyric acid chain, and the 4-aldehyde is reductively aminated with the protected diazabicyclononane 4. The reactions described above may then be carried out on the attached diazabicyclononane, which may be cleaved from the support by 1:1 trifluoroacetic acid in dichloromethane. [See PCT application WO97/23508.]

The materials upon which combinatorial syntheses are performed are referred to as solid supports, beads, and resins. These terms include: (a) beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have surfaces that have been functionalized with amino, hydroxy, carboxy, or halo groups; amino groups are most common. Techniques for functionalizing the surface of solid phases are well known in the art. Attachment of lysine to the surface of a bead (to increase the number of available sites) and subsequent attachment of linkers as well as further steps in a typical combinatorial synthesis are described, for example, in PCT application WO95/30642, the disclosure of which is incorporated herein by reference. When used herein, the term "solid substrate" or "residue of a solid substrate" includes both the base resin, bead etc (usually referred to as the solid support) and the linker.

According to Still et al., templates for synthetic receptors desirably have limited conformational mobility and have their functionality oriented in such a way that the receptor "arms", usually variable oligomeric chains, are directed toward nearby regions of space. The diazabicyclononane I of the invention is thus well suited as a template for a synthetic receptor or a library of synthetic receptors. Synthetic receptors may (a) bind an acceptor molecule; (b) exhibit biological activity; (c) catalyze a reaction; (d) inhibit a catalyzed reaction; or (e) function as a stationary phase in chromatography. A substrate of interest, detectable at nanomolar levels by way of its color, its fluorescence, its radioactivity, etc., may be prepared. Such detectable substrates are referred to herein as labeled substrates. A synthetic receptor library may be assayed to find those members of the library which have the desired interaction with the labeled substrate. In the case where the desired interaction is binding to the substrate, the synthetic receptor library is mixed with a solution of the labeled substrate and those library members that bind to the labeled substrate are selected. This procedure is particularly simple when the synthetic receptor library members are bound to a solid support. Solid support particles having receptors which bind the labeled substrate accumulate color or fluorescence or radioactivity (depending on the nature of the label used). Depending on the concentration of the labeled substrate used, the assay can be adjusted to detect binding of any desired strength: for example, if the amount of labeled substrate in the presence of the receptor library is adjusted to give a 100 µM concentration of free (unbound) labeled substrate, then assay will only detect template-substrate binding with association constants (k) of $(100\ \mu M)^{-1}$ or greater. Libraries of synthetic receptors may be similarly assayed for synthetic receptor(s) that catalyze a reaction or inhibit an enzyme-catalyzed reaction. The receptor libraries can also be used to find receptors to detect a drug, for example, an illicit drug.

Although their primary use is envisioned in the creation of libraries on solid supports, synthetic receptors incorporating the scaffold of the invention can also be used in affinity chromatography [Eveleigh, J. W. & Levy, D. E. Immunochemical characteristics and preparative application of agarose-based immunosorbents, *J. Solid Biochem.* 2, 45–78 (1977)]. Any gel may be used that offers the possibility of attaching the carboxylic acid residue. Thus gels that have amine and hydroxyl functionalities are particularly suitable. The scaffold is attached by methods well known in the art for preparing affinity gels.

A library is synthesized using combinatorial techniques. The synthetic receptor library may be prepared by any of the known methods for combinatorial synthesis [G. Jung and A. G. Beck-Sickinger, *Angew. Chem. Int. Ed.* 31, 367—383 (1992); Pavia et al., *Bioorg. Med. Chem. Lett.* 3, 387—396 (1993)]. Combinatorial synthetic techniques include the multi-pin method [Geysen et. al., *Proc. Natl. Acad. Sci. USA* 81, 3998 (1984); Geysen et al., *Proc. Natl. Acad. Sci. U.S.A.* 82, 178 (1985); WO 84/03564; WO 86/06487; WO 86/00991; and U.S. Pat. No. 5,133,866], the tea-bag method [U.S. Pat. No. 4,631,211; Houghton et al., *Int. J. Peptide Protein Res.* 27, 673 (1986); Houghton et al., *Biotechniques* 4, 522–528 (1986); Houghten, *Proc. Natl. Acad. Sci. USA* 82, 5131 (1985); WO 92/09300], the cellulose-paper method [Frank and Doering *Tetrahedron Lett.* 44, 6031 (1988)], the light-directed method (also termed as VLSIPS method,) [Fodor et. al., *Science* 251, 767 (1991); U.S. Pat. No. 5,143,854; WO 90/15070; WO 92/10092] and the split-synthesis method [Lam et al. *Nature* 354; 82 (1991); WO 92/00091, WO 93/06121]. The procedure for split synthesis involves creating a large library consisting of thousands to billions of different putative receptor molecules attached to particles such as beads, with each bead containing a single oligomer sequence and with the collection representing numerous combinations of possible random oligomer sequences.

The "one-bead, one-oligomer sequence" concept can be achieved easily by separating and mixing beads during the synthesis. For structure elucidation, readable tags (oligonucleotide tag or peptide tag) are cosynthesized to encode the series of steps and reagents used in the synthesis of each library element [Brenner and Lerner, *Proc. Natl. Acad. Sci, USA* 89 5381 (1992); Kerr et. al., *J. Am. Chem. Soc.* 115, 2529 (1993)]. Once a library element is selected by certain assay, its structure can be identified by its tag. The preferred encoding method is that of Ohlmeyer et al., as described in [*Proc. Natl. Acad. Sci. USA,* 90, 10922–10926 (1993); and PCT application WO 94/08051]. This technique makes use of highly sensitive, chemically inert molecular tags and a binary encoding scheme to provide a practical solution for the construction of large, chemically diverse libraries.

ABBREVIATIONS AND DEFINITIONS

The following abbreviations and terms have the indicated meanings when they occur; all of the abbreviations do not necessarily occur in this application:

| Ac | = | acetyl |
|---|---|---|
| Alloc | = | allyloxycarbonyl |
| Bn | = | benzyl |
| BNB | = | 4-bromomethyl-3-nitrobenzoic acid |
| Boc | = | t-butyloxy carbonyl |
| Bu | = | butyl |
| c- | = | cyclo |
| DCM | = | dichloromethane = methylene chloride = $CH_2Cl_2$ |
| DIC | = | diisopropylcarbodiimide |
| DIEA | = | N,N-diisopropylethyl amine |
| DMAP | = | 4-N,N-dimethylaminopyridine |
| DMF | = | N,N-dimethylformamide |
| DMSO | = | dimethyl sulfoxide |
| EEDQ | = | 2-ethoxy-1-ethoxycarbonyl-1,2-dihydroquinoline |
| Fmoc | = | 9-fluorenylmethoxycarbonyl |

-continued

| HATU | = | O-(7-Azabenzotriazol-1-yl)-1,1,3,3-tetramethyluronium hexafluorophosphate |
|---|---|---|
| HOAc | = | acetic acid |
| HOBt | = | hydroxybenzotriazole |
| Me | = | methyl |
| mesyl | = | methanesulfonyl |
| PEG | = | polyethylene glycol |
| Ph | = | phenyl |
| pyr | = | pyridine |
| rt | = | room temperature |
| sat'd | = | saturated |
| s- | = | secondary |
| t- | = | tertiary |
| TFA | = | trifluoroacetic acid |
| THF | = | tetrahydrofuran |

The invention claimed is:

1. A compound of formula

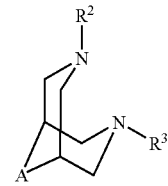

wherein A is CH—$NHR^1$;

$R^1$ is hydrogen or the residue of a solid substrate;

$R^2$ is hydrogen or a first amino-protecting group chosen from t-butoxycarbonyl, allyloxycarbonyl, benzyloxycarbonyl, fluorenylmethoxycarbonyl, benzyl and α-phenylethyl;

$R^3$ is hydrogen or a second amino-protecting group chosen from t-butoxycarbonyl, allyloxycarbonyl, benzyloxycarbonyl, fluorenylmethoxycarbonyl, benzyl and α-phenylethyl, with the proviso that no more than one of $R^1$, $R^2$ and $R^3$ is hydrogen.

2. A compound according to claim 1 wherein $R^1$ is the residue of a solid substrate, one of $R^2$ and $R^3$ is hydrogen and the other is chosen from t-butoxycarbonyl, allyloxycarbonyl, benzyloxycarbonyl and fluorenylmethoxycarbonyl.

3. A compound according to claim 1 wherein one of $R^2$ and $R^3$ is t-butoxycarbonyl and the other is chosen from allyloxycarbonyl, benzyloxycarbonyl, and fluorenylmethoxycarbonyl.

4. A compound according to claim 3 wherein $R^2$ is t-butoxycarbonyl and $R^3$ is allyloxycarbonyl.

5. A compound of formula

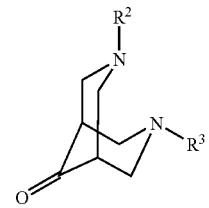

wherein

R² and R³ are chosen from t-butoxycarbonyl, allyloxycarbonyl, benzyloxycarbonyl, and fluorenylmethoxycarbonyl.

6. A compound according to claim 5 wherein one of R² and R³ is t-butoxycarbonyl and the other is chosen from allyloxycarbonyl, benzyloxycarbonyl, and fluorenylmethoxycarbonyl.

7. A compound according to claim 6 wherein R² is t-butoxycarbonyl and R³ is allyloxycarbonyl.

8. A compound of formula

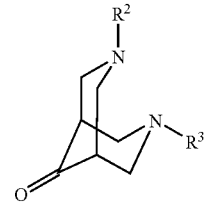

wherein one of R² and R³ is hydrogen and the other is chosen from allyloxycarbonyl, benzyloxycarbonyl and fluorenylmethoxycarbonyl.

* * * * *